United States Patent [19]

Santoro et al.

[11] Patent Number: 5,171,330

[45] Date of Patent: Dec. 15, 1992

[54] COMPOSITIONS OF REFINERY HYDROCARBONS ENDOWED WITH IMPROVED FLUIDITY AT LOW TEMPERATURES CONTAINING METHACYCLOPHANES

[75] Inventors: Ettore Santoro, Paderno Dugnano; Luciano Canova, Novara; Enrico Dalcanale, Parma; Stefanio Bonsignore, Novara; Paolo Falchi, Chieti, all of Italy

[73] Assignee: Societa' Italiana Additivi Per Carburanti, Pescara, Italy

[21] Appl. No.: 711,763

[22] Filed: Jun. 7, 1991

[30] Foreign Application Priority Data

Jun. 8, 1990 [IT] Italy ............................ 20596A/90

[51] Int. Cl.⁵ .............................................. C10L 1/18
[52] U.S. Cl. ........................................ 44/437; 44/440; 44/441; 44/442
[58] Field of Search ............... 44/437, 440, 441, 442; 568/632, 633, 640, 641; 560/73, 101, 140

[56] References Cited

U.S. PATENT DOCUMENTS

| 2,034,024 | 3/1936 | Clark | 44/437 |
| 2,801,926 | 8/1957 | Thompson | 426/546 |
| 4,434,265 | 2/1984 | Chasar | 568/640 |
| 4,617,336 | 10/1986 | Pastor | 560/75 |
| 4,662,414 | 11/1986 | McKervey | 568/325 |
| 4,718,966 | 1/1988 | Harris | 568/633 |
| 4,918,217 | 4/1990 | Dal Canale | 560/73 |

FOREIGN PATENT DOCUMENTS

| 350842 | 10/1987 | European Pat. Off. . |
| 300800 | 7/1988 | European Pat. Off. . |
| 311452 | 10/1988 | European Pat. Off. . |
| 339826 | 4/1989 | European Pat. Off. . |
| 400773 | 2/1990 | European Pat. Off. . |
| 409403 | 6/1990 | European Pat. Off. . |
| 264445 | 10/1987 | Fed. Rep. of Germany . |
| 264446 | 10/1987 | Fed. Rep. of Germany . |
| 1167427 | 12/1967 | United Kingdom . |

Primary Examiner—Prince Willis, Jr.
Assistant Examiner—Thomas Steinberg
Attorney, Agent, or Firm—Morgan & Finnegan

[57] ABSTRACT

The fluidity at low temperatures of compositions based on refinery liquid hydrocarbons can be improved by adding, preferably under solution, [I₄]-methacyclophanes with substituents, obtained from the condensation reaction of a resorcin with a product containing an aldehyde group, followed by a reaction with halides of organic acids or alkyl halides.

8 Claims, No Drawings

COMPOSITIONS OF REFINERY HYDROCARBONS ENDOWED WITH IMPROVED FLUIDITY AT LOW TEMPERATURES CONTAINING METHACYCLOPHANES

The present invention relates to compositions based on refinery liquid hydrocarbons, such as gas oils and fuel oil and, more in general, products known as Middle Distillate which, on lowering the temperature, present undesired physical changes which are detected by measuring the following parameters: Cloud Point (C.P.) Pour Point (P.P.) and Cold Filter Plugging Point (C.F.P.P.) as defined respectively in the ASTM D2500-81, ASTM D97-85 and IP 309/83.

The term Middle Distillate means hydrocarbon fractions having a distillation range of from 150° to 450° C. (ASTM D86-67.

BACKGROUND OF THE INVENTION

It is well-known, for example, that the fluidity of gas oils used for motor vehicles, for naval and aircraft engines or for heating, decreases when the temperature lowers, causing quite serious inconveniences.

The above phenomenon is mainly due to the precipitation of n-paraffins contained in the gas oil.

It is also well-known that such inconveniences can be overcome by the addition to the above hydrocarbons of suitable products, normally polymeric substances.

The additives which are normally used for this purpose are ethylene/vinylacetate copolymers of a particular molecular weight and composition, or ethylene/propylene/unconjugated diene copolymers and terpolymers, prepared by using homogeneous catalysts (based on vanadium and aluminium organometallic compounds) as described in the Italian patents N. 811,873 and 866,519.

The U.S. Pat. Nos. 3,374,073 and 3,756,954 propose as additives the ethylene/propylene/conjugated or unconjugated diene terpolymers, prepared by using homogeneous catalysts, which suffered degradation to certain values of molecular weight, through thermal oxidation.

The most common additives for gas oil or Middle Distillate allow the use of these hydrocarbons also at low temperatures in that, by interfering on the crystallization kinetics, they determine the form and dimensions of the crystals and also restrain the crystallization and agglomeration of crystals, thus improving the liquid flow. Said additives, therefore, do not modify the cloud point of the hydrocarbon compounds, i.e. the temperature of the first appearance of the paraffin crystals in the liquid.

DESCRIPTION OF THE INVENTION

The Applicant has found a number of additives for Middle Distillate which lower the Cloud Point of said hydrocarbon fractions in that they inhibit the formation of the crystalline nucleus of paraffins. Such nucleus, therefore, is formed at a lower temperature than in paraffins without said additives.

Therefore, the present invention concerns compositions of refinery hydrocarbons which include at least one additive lowering the Cloud Point, having the general formula:

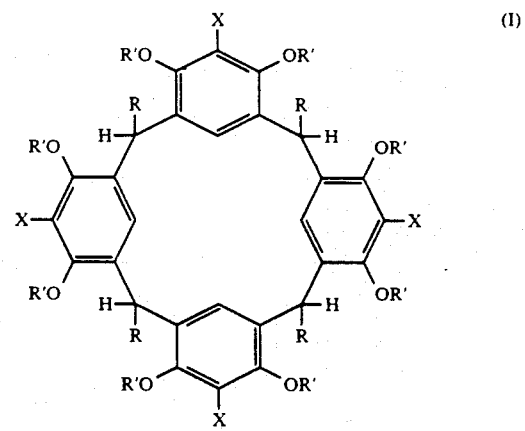

where R is an alkyl radical, iso-alkyl, cyclo-alkyl, aryl, alkyl-aryl $C_1$–$C_{30}$ radicals, R', whether alike or different, is an alkyl radical, iso-alkyl, cyclo-alkyl, aryl, alkyl-aryl $C_1$–$C_{30}$ radicals, or one of the radicals having the following general formula:

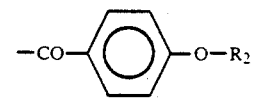

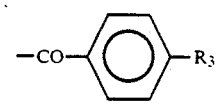

where $R_1$, $R_2$, $R_3$, whether alike or different, are an alkyl radical, iso-alkyl, cyclo-alkyl, aryl, alkyl-aryl $C_1$–$C_{30}$ radicals, and X is a hydrogen atom, an alkyl radical with a low number of carbon atoms, for example $C_1$–$C_4$, or an —OR' group in which R' has the above mentioned meaning.

Examples of products having general formula I and particularly suitable as additives lowering the Cloud Point of the compositions of the present invention, are:

3.5.10.12.17.19.24.26-octaoctadecanoyloxy-r-1,c-8,c-15,c-22-tetraenaicosan-[l4] methacyclophane;

3.5.10.11.12.17.18.19.24.25.26-dodeca-exadeciloxy-r-1,c-8, c-15,c-22-tetramethyl-[l4] methacyclophane;

3.4.5.10.11.12.17.18.19.24.25.26-dodeca-octadecanoyloxy-r-1, c-8,c-15,c-22-tetraundecil-[l4] methacyclophane;

4.11.18.25-tetramethyl-3.5.10.12.17.19.24.25.26-octadodecanoyl-oxy-[l4]methacyclophane;

4.11.18.25-tetramethyl-3.5.10.12.17.19.24.26-octaoctadecanoyl-oxy-[l4]methacyclophane;

3.5.10.12.17.19.24.26-octa-acetyloxy-r-1,c-8,c-15, c-22-tetraeptadecyl-[l4]methacyclophane;

3.5.10.12.17.19.24.26-octa-octadecanoyloxy-r-1,c-8,c-15,c-22-tetramethyl-[l4]methacyclophane;

3.5.10.12.17.19.24.26-octa-dodecanoyloxy-r-1,c-8,c-15,c-22-tetramethyl-[l4]methacyclophane;

3.5.10.12.17.19.24.26-octa-tetradecanoyloxy-r-1,c-8,c-15,c-22-tetramethyl-[l4]methacyclophane;

3.5.10.12.17.19.24.26-octa-p-dodecyloxybenzoyloxy-r-1,c-8,c-15,c-22-tetramethyl-[l4]methacyclophane;

3.5.10.12.17.19.24.26-octa-exanoyloxy-r-1,c-8,c-15,c-22-tetraethyl-[l4]methacyclophane;

3.5.10.12.17.19.24.26-octa-decanoyloxy-r-1,c-8,c-15,c-22-tetraethyl-[l4]methacyclophane;

3.4.5.10.11.12.17.18.19.24.25.26-dodecatridecanoyloxy-r-1,c-8,c-15,c-22-tetramethyl-[l4]methacyclophane;

3.4.5.10.11.12.17.18.19.24.25.26-dodeca-tetradecanoyloxy-r-1,c-8,c-15,c-22-tetramethyl-[l4]methacyclophane;

3.4.5.10.11.12.17.18.19.24.25.26.-dodecaexadecanoyloxy-r-1,c-8,c-15,c-22-tetramethyl-[l4]methacyclophane;

3.4.5.10.11.12.17.18.19.24.25.26-dodeca-octadecanoyloxy-r-1,c-8,c-22-tetramethyl-[l4]methacyclophane;

3.4.5.10.11.12.17.18.19.24.25.26-dodecadodecadodecanoyloxy-r-1,c-8,c-15,c-22-tetraethyl-[4]methacyclophane;

3.4.5.10.11.12.17.18.19.24.25.26-dodecadecanoyloxy-r-1,c-8,c-15,c-22-tetraethyl-[l4]methacyclophane, etc.

The tetramers having formula (I) can be synthesized by reacting a resorcin, possibly substituted in position 2, with an aldehyde and subsequent esterification of the product obtained. The reaction between resorcin and aldehyde occurs following the reaction scheme:

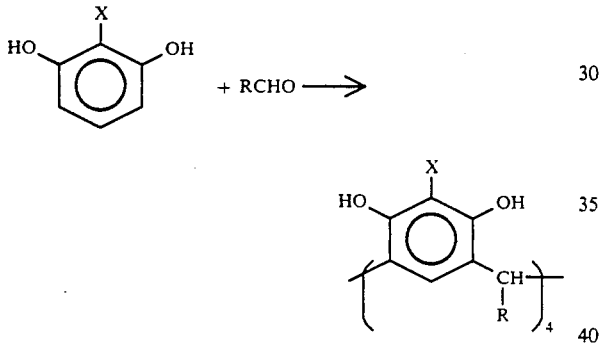

where X and R have the above-specified meaning, followed by esterification preferably with organic acid halides or alkyl halides.

Examples of resorcines are resorcinol, pyrogallol, 2,6-di-hydroxy-toluene, etc.

Examples of molecules with an aldehydic group which can be used in the synthesis of the products of the present invention are: formaldehyde, acetaldehyde, laurylaldehyde, enanthic aldehyde, benzaldehyde, 1-docosanol, stearic aldehyde, palmitic aldehyde, 1-decanol, etc.

The synthesis is generally carried out at room temperature, in a solvent, preferably methanol or ethanol, and in the presence of an acid catalyst.

Examples of catalysts are hydrogen chloride, sulphuric acid, phosphoric acid, para-toluenesulfonic acid, etc. possibly diluted in water at a concentration from 25 to 50% by weight.

These catalysts are used in quantities of between 1 and 20% by weight of the total amount of the reagents.

The products thus obtained, recovered from the solvent by means of well-known techniques, for example by evaporation or precipitation using non-solvents, are esterified either with at least one halide having the formula R'-Al, where R' has the above-mentioned meaning and Al is a halogen such as chlorine or bromine, or with an anhydride.

Examples of halides according to the present invention are: acetyl chloride, lauroyl chloride, palmitoyl chloride, stearoyl chloride, myristoyl chloride, decanoyl chloride, tridecanoyl chloride, 1-bromohexadecane, 1-bromodecane, 1-bromododecane, etc.

In particular, the reaction with the compound having formula R'-Al, where R' is an alkyl, or iso-alkyl, cycloalkyl, aryl, alkyl-aryl $C_1$–$C_{30}$ radical, is carried out preferably in an organic solvent, such as dimethylformamide (DMF) or dimethylsulfoxide (DMSO) and in the presence of an organic base such as potassium carbonate.

Among the compounds having formula (I), the substituted [l4]-methacyclophanes of general formula:

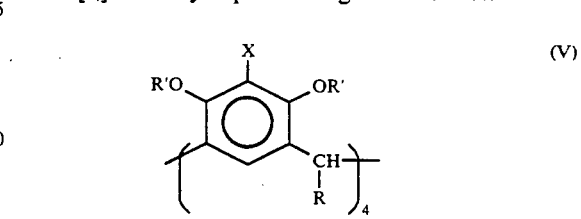

where X can be:
i) a hydrogen atom, and therefore: R is a linear alkyl radical $C_4$–$C_{30}$, or an iso-alkyl, cycloalkyl, aryl, alkyl-aryl $C_3$–$C_{30}$ radicals, and the R' radicals, either alike or different, represent a group:

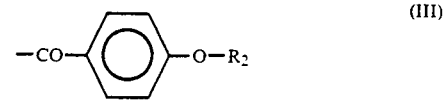

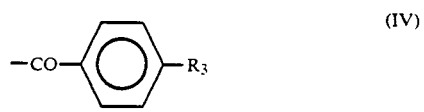

where $R_1$, $R_2$ and $R_3$, either alike or different, are an alkyl, iso-alkyl, cyclo-alkyl, aryl, alkyl-aryl $C_1$–$C_{30}$ radical;

ii) an alkyl radical having a low number of carbon atoms, for example $C_1$–$C_4$ and therefore: R is a hydrogen atom or an alkyl, iso-alkyl, cyclo-alkyl, aryl, alkyl-aryl $C_1$–$C_{30}$ radical and R' represents a group chosen from among those having formula (II), (III) and (IV), where $R_1$, $R_2$ and $R_3$, either alike or different, are an alkyl, iso-alkyl, cyclo-alkyl, aryl, alkyl-aryl $C_1$–$C_{30}$ radical;

iii) an OR' group, and therefore: R is an alkyl, iso-alkyl, cyclo-alkyl, aryl, alkyl-aryl $C_3$–$C_{30}$ radical and R' represents a group chosen from among those having formula (II), (III) and (IV), as defined in (i) and (ii) hereabove;

iv) an OR'' group, and therefore: R is an alkyl, iso-alkyl, cyclo-alkyl, aryl, alkyl-aryl $C_1$–$C_{30}$ radical and R' and R'', alike among them, are an alkyl, iso-alkyl, cyclo-alkyl, aryl, alkyl-aryl $C_1$–$C_{30}$ radical;

are new products and have never been described in any previous literature. These products can be obtained using the same method previously described.

The anti-cloud additives having the general formula (I) can be added to the gas oils or to the hydrocarbon fractions known as Middle Distillate, either directly or dissolved in solvents, preferably high-boiling aromatic, such as the products available on the market under the trade-name of SHELLSOL AB, SHELLSOL A, E, R, SOLVESSO 100, 150, 200, HAN, etc., either as such or mixed with other additives like antioxidants, basic detergents, rust inhibitors, pour-point depressants, etc.

These additives can be added to the hydrocarbon fractions in quantities which are higher than 0.001% by weight, generally between 0.001 and 1%, preferably between 0.005 and 0.15%.

The hydrocarbon fractions containing the tetramers having the general formula (I) show a lowering in the cloud-point of more than 10° C.

It must be noted that the above tetramers have the property of inhibiting the sedimentation of paraffins during storage as well as the corrosion of metal surfaces in contact with the treated hydrocarbon fractions.

EXAMPLES

In order to enable a clearer interpretation and to allow the practical enforcement of the present invention, the following examples are listed as an illustration of said invention but without limiting it in any way.

To evaluate the anti-cloud properties of the present tetramers, hydrocarbon fractions having the characteristics shown in Table 1 were taken into consideration.

TABLE 1

| | CHARACTERISTICS | | |
|---|---|---|---|
| | DISTILLATION RANGE ASTM D86-82 TEMPERATURE °C. | | TEMPERATURE °C. CORRESPONDING TO 90% BY VOLUME | DENSITY AT 15° C. |
| FRACTIONS | FROM | TO | OF DISTILLATE | Kg/l |
| A | 179 | 385 | 357 | 0.8466 |
| B | 191 | 370 | 343 | 0.8595 |
| C | 194 | 369 | 342 | 0.8449 |

The tests relate to the following properties of the hydrocarbon fractions:
C.P. = Cloud-Point according to ASTM 2500-81
C.F.P.P. = Cold-Filter Plugging Point according to IP 309/83
P.P. = Pour-Point according to ASTM D97-66.

EXAMPLE 1

Preparation of 3.5.10.12.17.19.24.26-octaoctadecanoiloxy-r-1,c-8,c-15,c-22-tetraenaicosan-[I$_4$] methacyclophane.

Part A:

1.65 g (15 mM) of resorcinol are dissolved under an argon atmosphere in 6 ml of ethanol and 3 ml of HCl at 37%. The solution is cooled down with an ice-bath to 5° C. and 4.87 g (15 mM) of 1-docosanol, dissolved in 70 ml of ethanol, are added in drops. The mixture is then reflux-heated for 8 hours. At the end it is cooled to room temperature. The precipitate obtained is filtered, washed with water until neutral, dried under vacuum (25° C./1×10$^{-3}$ mmHg) and finally crystallized from ethanol. 4.31 g of pure tetramer are obtained (69% yield).

$^1$H-NMR (CDCl$_3$): 0,90 (t, 12H, CH$_3$); 1,28 |bs,152H,(CH$_2$)$_{19}$|; 2,31 (bm,8H,CH—CH$_2$); 4,33 (t,4H,CH); 6,14 (s,4H,Ar—H$_a$); 7,23 (s,4H,Ar—H$_b$); 9,20 (s,4H,OH$_a$); 9,50 (s,4H,OH$_b$).

Elementary analysis for C$_{112}$H$_{192}$O$_8$; theoretical C=80.71%; H=11.61% experimental C=81.05% H=12.00%

Part B 0.420 g (0.25 mM) of the tetramer thus obtained and 3.02 g (10 mM) of stearoyl chloride are heated for 8 hours at 150° C. under magnetic stirring.

At the end of the reaction the excess chloride is distilled under vacuum (140 ° C./1×10$^{-2}$ mmHg).

The remaining residue is dissolved in methylene chloride and the solution obtained is extracted with NaOH 0.2N, then washed with water until neutral and finally dehydrated on anhydrous sodium sulphate.

The solvent is evaporated and the remaining residue is passed on a silica gel column with hexane/methylene chloride 65/35 as an eluent. 0.62 g of pure product are obtained (65% yield).

Mass (DCI−): M$^-$-CO-C$_{17}$H$_{35}$=3527 (2 $^{13}$C).

$^1$H-NMR (CDCl$_3$): 0,86[m,36H,(CH$_2$)$_n$—CH$_3$)]; 1,26{bs,376H, 2x [(CH$_2$)$_{14}$]+(CH$_2$)$_{19}$}; 1,45 (m,8H,CH—CH$_2$); 1,64 (m,16H,CO—CH$_2$—CH$_2$); 2,25 (m,8H,CO—CH$_2$); 2,56 (m, 8H, CO—CH$_2$'); 4,09 (t,4H,CH); 5,99 (s,2H,Ar—H$_a$); 6,70 (s,2H,Ar—H$_b$); 6,73 (s,2H,Ar—H$_b$'); 7,21 (s,2H,Ar—H$_a$').

Elementary analysis for C$_{256}$H$_{464}$O$_{16}$; theoretical C=80.95%; H=12.31% experimental C=81.20% H=12.57%

The product thus obtained, dissolved in SHELLSOL AB solvent (10% concentration), was added to the hydrocarbon fractions specified in Table 1 in the quantities shown.

The following Table 2 shows the final results.

TABLE 2

| CONCENTRATION (ppm) | HYDROCARBON FRACTION | | | | | |
|---|---|---|---|---|---|---|
| | A | | | B | | |
| | CP | CFPP | PP | CP | CFPP | PP |
| 0 | 3 | 3 | −6 | −4 | −5 | −12 |
| 100 | 1 | 4 | −12 | −5 | −4 | −15 |
| 175 | 1 | 2 | −12 | −6 | −4 | −15 |

EXAMPLE 2

Preparation of 3.4.5.10.11.12.17.18.19.24.25.26-dodecaexadeciloxy-r-1,c-8,c-15,c-22-tetramethyl-[I$_4$] methacyclophane.

0.609 g (1 mM) of a tetramer obtained as described in Example 1, Part A, with the exception that the 1-docosanol is substituted by acetaldehyde and resorcinol by pirogallol, are dissolved in 50 ml of anhydrous DMF.

12.21 g (40 mM) of 1-bromohexadecane and 7.19 g (54 mM) of potassium carbonate are added to the solution. The mixture is heated to 80° C. for 48 hrs. At the end of the reaction, the mixture is diluted in water and extracted with ethyl ether. The organic phase is then separated, washed with water until neutral and dehydrated on anhydrous sodium sulphate. The solvent is evaporated and the residue is purified on a silica gel column (two successive purifications are carried out, the first using hexane/methylene chloride 7/3 as the eluent and the second hexane/methylene chloride 75/25). 1.45 g of pure product are obtained (44% yield).

Mass (DCI+): M+ =3298 (2 $^{13}$C).

$^1$H-NMR (CDCl$_3$): 0,86 [t,36H,(CH$_2$)$_n$—CH$_3$]; 1,24 [bs,312H, (CH$_2$)$_{13}$]; 1,40 (m,12H,O—CH$_2$—CH$_2$); 1,51 (d,12H, J=7,4 Hz,CH—CH$_3$); 1,61 (m,12H,O—CH$_2$—CH$_2$'); 3,12 (m,4H,O—CH$_2$); 3,61 (m,8H,O—CH$_2$'); 4,07 (m,12H,O—CH$_2$''); 4,58 (q,4H, J=7,4 Hz,CH); 5,67 (s,2H,Ar—H); 6,97 (s,2H,Ar—H').

Elementary analysis for C$_{224}$H$_{416}$O$_{12}$; theoretical C=81.48%; H=12.70% experimental C=81.35% H=12.81%

The product thus obtained, dissolved in SHELLSOL AB solvent (10%), was added to the hydrocarbon fractions specified in Table 1.

The following Table 3 shows the final results.

TABLE 3

| CONCENTRATION (ppm) | HYDROCARBON FRACTION | | | | | | | | |
|---|---|---|---|---|---|---|---|---|---|
| | A | | | B | | | C | | |
| | CP | CFPP | PP | CP | CFPP | PP | CP | CFPP | PP |
| 0 | 3 | 3 | −6 | −4 | −5 | −12 | −1 | −2 | −9 |
| 100 | 3 | 6 | −15 | −6 | −5 | −12 | −5 | — | −9 |
| 175 | 1 | 4 | −18 | −7 | −7 | −12 | −4 | — | −12 |
| 350 | — | — | — | — | — | — | −4 | — | −12 |

EXAMPLE 3

Preparation of 3.4.5.10.11.12.17.18.19.24.25.26-dodeca-octadecanoiloxy-r-1,c-8,c-15,c-22-tetraundecyl-[l$_4$] methacyclophane.

Part A:

3.03 g (24 mM) of pyrogallol are dissolved under an argon atmosphere in 20 ml of ethanol and 3 ml of HCl 37%. The solution is cooled in an ice and salt bath to 0° C. and 4.42 g (24 mM) of laurylaldehyde are added in drops. The solution is kept at room temperature under stirring for 24 hrs and is then reflux-heated for 4 hrs. It is then cooled slowly to room temperature. The precipitate obtained is filtered, washed with water until neutral and crystallized from ethanol. The solid product thus obtained is filtered and dried under vacuum (25° C./1×10$^{-5}$ mmHg). 1.60 g of product containing two ethanol molecules for each tetramer molecule, are obtained.

$^1$H-NMR (acetone-d$_6$): 0,88 (t,12H,CH$_3$) 1,31 [bs,72H,(CH$_2$)$_9$]; 2,28 (m,8H,CH—CH$_2$); 4,35 (t,4H,CH); 7,09 (s,4H,Ar—H); 9,20 (bs,4H,OH$_a$); 9,45 (bs,8H,OH$_b$).

Elementary analysis for C$_{72}$H$_{112}$O$_{12}$x2C$_2$H$_5$OH; theoretical C=72.34%; H=9.91% experimental C=72.38% H=9.81%

Part B:

Following the method described in Example 1, the above product was obtained with a 60% yield, after purification on a silica gel column, using hexane/methylene chloride 7/3 as the eluent.

Mass (DCI−): M− =4363 (3 $^{13}$C)

$^1$H-NMR (CDCl$_3$): 0,86 (m,48H,(CH$_2$)$_n$—CH$_3$); 1,30 {bs,408H, 3x(CH$_2$)$_{14}$+(CH$_2$)$_9$}; 1,45 (m,8H,CH—CH$_2$); 1,61 (m,24H, CO—CH$_2$—CH$_2$); 2,25 (m,12H,CO—CH$_2$); 2,47 (m,12H,CO—CH$_2$'); 4,08 (t,4H,CH); 6,02 (s,2H,Ar—H); 7,21 (s,2H,Ar—H').

Elementary analysis for C$_{228}$H$_{520}$O$_{24}$; theoretical C=79.20%; H=12.00% experimental C=79.52% H=12.29%

The product thus obtained, dissolved in SHELLSOL AB solvent (10%), was added to the hydrocarbon fractions specified in Table 1.

The following Table 4 shows the final results.

TABLE 4

| CONCENTRAT. (ppm) | HYDROCARBON FRACTION | | | | | | | | |
|---|---|---|---|---|---|---|---|---|---|
| | A | | | B | | | C | | |
| | CP | CFPP | PP | CP | CFPP | PP | CP | CFPP | PP |
| 0 | 3 | 3 | −6 | −4 | −5 | −12 | −1 | −2 | −9 |
| 100 | 1 | 2 | −9 | −7 | −5 | −12 | −4 | — | −12 |
| 175 | 1 | 1 | −9 | −7 | −5 | −12 | −4 | — | −12 |

EXAMPLE 4

The same procedure is used as in Example 2 with the exception that the tetramer obtained in the first part is reacted with an equimolar mixture of the following acid chlorides: lauryl chloride, palmitoyl chloride, stearoyl chloride, docosanoyl chloride. A mixture of substituted products having a molecular weight of between 2792 and 4472 is obtained, after purification on a silica gel, with methylene chloride/hexane 8/2 as eluent.

The mixture of products thus obtained, dissolved in SHELLSOL AB (10%), was added to the hydrocarbon fractions of Table 1. The following Table 5 shows the final results.

TABLE 5

| CONCENTRATION (ppm) | HYDROCARBON FRACTION | | | | | |
|---|---|---|---|---|---|---|
| | A | | | B | | |
| | CP | CFPP | PP | CP | CFPP | PP |
| 0 | 3 | 3 | −6 | −4 | −5 | −12 |
| 100 | 3 | 4 | −12 | −5 | −2 | −15 |
| 175 | 3 | 3 | −15 | −5 | −3 | −18 |

EXAMPLE 5

Preparation of 4.11.18.25-tetramethyl-3.5.10.12.17. 19.24.26.26-octa-dodecanoyloxy-[l$_4$] methacyclophane.

Part A:

37.3 g (300 mM) of 2,6-dihydroxytoluene are dissolved, under an argon atmosphere, in 120 ml of degassed ethanol and 30 ml of 37% HCl. The solution is cooled to 5° C. in an ice-bath and 25.7 ml (326 mM) of 35% formaldehyde in water are added in drops for two hours. The solution is left at room temperature for 48 hours and is then reflux-heated for 6 hours. After cooling, a precipitate is obtained which is then filtered. On adding water to the solution a further precipitate is obtained. The two precipitates are mixed, washed with water until neutral and crystallized from acetone. The precipitate thus obtained is filtered and dried under vacuum (25° C./1×10$^{-5}$ mmHg). 25.0 g of product are obtained (61% yield).

$^1$H-NMR (DMSO-d$_6$): 2,08 (s,12H,CH$_3$); 3,67 (s,8H,CH$_2$); 6,82 (s,4H,Ar—H); 8,68 (s,8H,OH).

Elementary analysis for C$_{32}$H$_{32}$O$_8$; theoretical C=70.57%; H=5.92% experimental C=70.19% H=5.62%

Part B:

With the same procedure described in Example 1, Part B, by using dodecanoyl chloride, the above product was obtained with a 75% yield, after double crystallization from acetone.

Mass (DCI+): MH+ =2002 (1 $^{13}$C)

$^1$H-NMR (CDCl$_3$): 0,89 (t,24H,(CH$_2$)$_n$—CH$_3$); 1,25 [bs,128H, (CH$_2$)$_8$]; 1.68 (m,16H,CO—CH$_2$—CH$_2$); 1,89 (s,12H,Ar—CH$_3$); 2.51 (t,16H,CO—CH$_2$); 3,50 (s,8H,Ar—CH$_2$—Ar); 6,38 (s,4H,Ar—H).

Elementary analysis for C$_{128}$H$_{208}$O$_{16}$; theoretical C=76.75%; H=10.47% experimental C=76.67% H=10.51%

The product thus obtained, dissolved in SHELLSOL AB solvent (10%) was added to the hydrocarbon fractions shown in Table 1.

The following Table 6 shows the final results.

TABLE 6

| CONCENTRAT. (ppm) | HYDROCARBON FRACTION B | | |
|---|---|---|---|
| | CP | CFPP | PP |
| 0 | −4 | −5 | −12 |
| 100 | −5 | −5 | −12 |
| 175 | −5 | −5 | −15 |
| 350 | −6 | −6 | −15 |

EXAMPLE 6

Preparation of 4.11.18.25-tetramethyl-3.5.10.12.17.19.24.26-octa-octadecanoyloxy-[l$_4$] methacyclophane.

The same procedure is used as in Example 1, Part B by reacting stearoyl chloride with the tetramer of Example 5, Part A. The above product was obtained with a 60% yield after purification on a silica gel column using methylene chloride/hexane 9/1 as eluent.

Mass (DCI+): M+ =2673 (1 $^{13}$C).

$^1$H-NMR (CDCl$_3$): 0,86 (t,24H,(CH$_2$)$_n$—CH$_3$); 1,24 [bs,224H, (CH$_2$)$_{14}$]; 1,66 (m,16H,CO—CH$_2$—CH$_2$); 1,88 (s,12H,Ar—CH$_3$); 2,47 (t,16H,CO—CH$_2$); 3,49 (s,8H,Ar—CH$_2$—Ar); 6,36 (s,4H,Ar—H).

Elementary analysis for C$_{175}$H$_{304}$O$_{16}$; theoretical C=78.98%; H=11.45% experimental C=78.88% H=11.62%

The product thus obtained, dissolved in SHELLSOL AB solvent (10%), was added to the hydrocarbon fractions of Table 1 The following Table 7 shows the final results.

TABLE 7

| CONCENTRAT. (ppm) | HYDROCARBON FRACTION | | | | | |
|---|---|---|---|---|---|---|
| | A | | | B | | |
| | CP | CFPP | PP | CP | CFPP | PP |
| 0 | 3 | 3 | −6 | −4 | −5 | −12 |
| 100 | 4 | 2 | −12 | −6 | −5 | −21 |
| 175 | 3 | 3 | −15 | −6 | −7 | −21 |

EXAMPLE 7

Preparation of 3.5.10.12.17.19.24.26-octa-acetyloxy-r-1,c-8,c-15,c-22-tetraeptadecyl-[l$_4$] methacyclophane.

Part A:

The same procedure has been used as in Example 1, Part A, using stearic aldehyde instead of 1-docosanol, with an 82% yield.

$^1$H-NMR (CD$_3$OD, 84° C.): 0,91 [t,12H,(CH$_2$)$_n$—CH$_3$)]; 1,36 [bs,120H, (CH$_2$)$_{15}$]; 2,16 (m,8H,CH—CH$_2$); 4,29 (t,4H,CH); 6,21 (s,4H,Ar—H$_a$); 7,16 (s,4H,Ar—H$_b$).

Elementary analysis for C$_{96}$H$_{160}$O$_8$ theoretical C=79.94%; H=11.18% experimental C=79.59% H=10.79%

Part B:

1.50 g (1.04 mM) are suspended in 10 ml of acetic anhydride containing two drops of piridine. The mixture is refluxheated under stirring, for an hour. The solid precipitate thus obtained, after cooling, is filtered, washed with water until neutral and crystallized from ethanol. The precipitate is dried under vacuum (1×10$^{-3}$ mmHg). 1.38 g of pure product are obtained (75% yield).

Mass (DCI+): MH+ =1778 (1 $^{13}$C).

$^1$H-NMR (CDCl$_{13}$,): 0,89 [t,12H, (CH$_2$)$_n$—CH$_3$)]; 1,29 [bs,120H, (CH$_2$)$_{15}$]; 1,84 (m,8H,CH—CH$_2$); 2,13 (bs,24H,CO—CH$_3$); 4,12 (t,4H,CH); 6,10 (s,4H,Ar—H$_a$); 6,89 (s,4H,Ar—H$_b$).

theoretical C=75.63%; H=9.97% experimental C=75.42% H=9.83%

The product thus obtained, dissolved in SHELLSOL AB solvent (10%), was added to the hydrocarbon fractions shown in Table 1. Table 8 herebelow shows the final results.

TABLE 8

| CONCENTRATION (ppm) | HYDROCARBON FRACTION | | | | | |
|---|---|---|---|---|---|---|
| | A | | | B | | |
| | CP | CFPP | PP | CP | CFPP | PP |
| 0 | 3 | 3 | −6 | −4 | −5 | −12 |
| 100 | 4 | 4 | −9 | −4 | −5 | −15 |
| 175 | 4 | 3 | −9 | −5 | −5 | −15 |
| 350 | 4 | 2 | −12 | −6 | −5 | −18 |

EXAMPLE 8

Preparation of 3.5.10.12.17.19.24.26-octa-octadecanoyloxy-r-1,c-8,c-15,c-22-tetramethyl-[l$_4$] methacyclophane:

0.545 g (1 mM) of tetramer obtained in the first part of Example 1, with the exception that acetaldehyde is used instead of 1-docosanol, and 19.5 g of stearoyl chloride are heated to about 180° C. for 6 hours under stirring. At the end of the reaction, the excess chloride is distilled under vacuum (140° C./1×10$^{-2}$ mmHg).

The remaining residue is dissolved in methylene chloride and the solution obtained is first mixed and shaken with NaOH 0.2N, then washed with water until neutral and finally dehydrated on anhydrous sodium sulphate. The solvent is evaporated and the remaining residue is passed for two hours on a silica gel column using methylene chloride/hexane 7/3 and dimethylene chloride/hexane 6/4 as eluents. 1.66 g of and dimethylene chloride/hexane 6/4 as eluents. 1.66 g of pure product are obtained (62% yield).

Mass (DCI+):M+ =2673 (1 $^{13}$C).

$^1$H-NMR (CDCl$_3$):0,87[t, 24H, (CH$_2$)$_n$—CH$_3$)]; 1,28 [bs, 224H, (CH$_2$)$_{14}$]; 1,43 (d, 12H, J=7,5 Hz, CH—CH$_3$); 1,51 (m, 8H, CO—CH$_2$—CH$_2$); 1,75 (m, 8H, CO—CH$_2$—CH$_2$'); 2,22 (m, 8H, CO—CH$_2$); 2,57 (m, 8H, CO—CH$_2$'); 4,22 (q, 4H, J=7,5 Hz, CH); 5,91 (s, 2H, Ar—Ha); 6,72 (s, 2H, Ar—Hb); 6,88 (s, 2H, Ar—Hb'); 7,38 (s, 2H, Ar—Ha').

Elementary analysis for C$_{176}$H$_{304}$O$_{16}$ theoretical C=78.98%; H=11.45% experimental C=78.80% H=11.38%

175 p.p.m. of the product thus obtained were added, after 10% dilution in SHELLSOL AB solvent, to the A and B hydrocarbon fractions and the Pour Point was decreased respectively from −6° to −18° C. and from −12° to −21° C. 350 p.p.m. of the same product, added to fraction C, reduced its Cloud Point from −1° to −4° C.

EXAMPLE 9

Preparation of 3.4.5.10.11.12.17.18.19.24.25.26-dodecaoctadecanoyloxy-r-1,c-8,c-15,c-22-tetramethyl-[I$_4$] methacyclophane:

0.609 g (1 mM) of tetramer obtained in the first part of Example 2 and 12.12 g (40 mM) of stearoyl chloride are reacted using the same procedure as in Example 8. In this case the product is purified by double crystallization from methylene chloride/ethylic ether (53% yield).

Mass (DCI$^-$):M$^-$ = 3802 (2 $^{13}$C)

$^1$H-NMR (CDCl$_3$):0,89[t, 36H, (CH$_2$)$_n$—CH$_3$)]; 1,30 [bs, 336H, (CH$_2$)$_{14}$]; 1,46 (d, 12H, J=7,4 Hz, CH—CH$_3$); 1,70 (m, 24H, CO—CH$_2$—CH$_2$); 2,30 (m, 12H, CO—CH$_2$); 2,51 (m, 12H, CO—CH$_2$'); 4,23 (q, 4H, J=7,4 Hz, CH); 6,03 (s, 2H, Ar—H); 7,30 (s, 2H, Ar—H').

Elementary analysis for C$_{248}$H$_{440}$O$_{24}$ theoretical C=78.26%; H=11.65% experimental C=78.30% H=11.70%

175 p.p.m. of the product thus obtained were added, after 10% dilution in SHELLSOL AB solvent, to the A hydrocarbon fractions and the Pour Point was decreased from 3° to 0° C.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Composition of refinery hydrocarbons comprising a refinery hydrocarbon fraction including at least one anti-cloud additive, said additive being added to said hydrocarbon fraction directly or by admixture with a suitable solvent and chosen among those having formula:

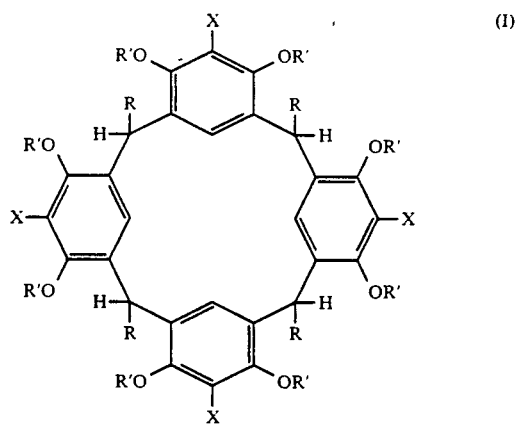

where R is an alkyl radical, iso-alkyl, cyclo-alkyl, aryl, alkyl-aryl C$_1$–C$_{30}$ radicals, R', whether alike or different, is an alkyl radical, iso-alkyl, cyclo-alkyl, aryl, alkyl-aryl C$_1$–C$_{30}$ radicals, or one of the radicals having the following formula:

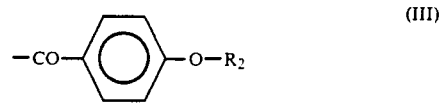

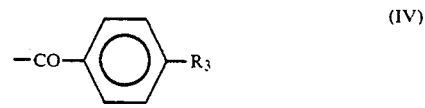

where R$_1$, R$_2$, and R$_3$, whether alike or different, are defined as follows: R$_1$ is an alkyl radical, iso-alkyl, cyclo-alkyl or an aryl radical, R$_2$ and R$_3$ can each be an alkyl, iso-alkyl, cyclo-alkyl, aryl or an alkyl-aryl C$_1$–C$_{30}$ radical, and X is a hydrogen atom, an alkyl radical with a low number of carbon atom or an —OR' group in which R' has the above mentioned meaning.

2. Composition according to claim 1, wherein the additives having formula (I) are synthesized by reacting a resorcin, optionally substituted in position 2, with an aldehyde and subsequent esterification of the product obtained with a halide having the formula R'-Al, where R' has the above-mentioned meaning and Al is a halogen, or with an anhydride.

3. Composition according to claim 1, wherein the additives are added to the hydrocarbon fractions in quantities greater than 0.001% by weight.

4. Composition according to claim 1, further comprising a decrease of the Cloud Point of up to 3° C. and of the Pour Point greater than 10° C.

5. Process for the preparation of hydrocarbon composition according to claim 1, comprising the addition of at least one additive having formula (I) in an amount greater than 0.001% by weight to a Middle Distillate.

6. Substituted-methacyclophanes of formula:

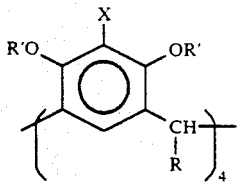

(V)

where X can be:

i) a hydrogen atom, and therefore:

R is a linear alkyl $C_4$–$C_{30}$ radical, an iso-alkyl, cyclo-alkyl, aryl or an alkyl-aryl $C_3$–$C_{30}$ radical, and the R′ radicals, whether alike or different, represent a group:

  (II)

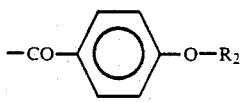  (III)

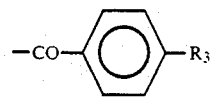  (IV)

where $R_1$, $R_2$, and $R_3$, whether alike or different, are defined as follows: $R_1$ is an alkyl, iso-alkyl, cyclo-alkyl or an aryl radical, and $R_2$ and $R_3$ can each be an alkyl, iso-alkyl, cyclo-alkyl, aryl or an alkyl-aryl $C_1$–$C_{30}$ radical;

ii) an alkyl radical having a low number of carbon atoms, and therefore:

R is a hydrogen atom or an alkyl, iso-alkyl, cyclo-alkyl, aryl or an alkyl-aryl $C_1$–$C_{30}$ radical and R′ represents a group chosen among those having formula (II), (III) and (IV), and $R_1$, $R_2$, and $R_3$, are defined in (i) hereabove;

iii) an OR′ group, and therefore:

R is an alkyl, iso-alkyl, cyclo-alkyl, aryl or an alkyl-aryl $C_3$–$C_{30}$ radical and R′ represents a group chosen from among those having formula (II), (III) and (IV), as defined in (i) hereabove;

iv) an OR″ group, and therefore:

R is an alkyl, iso-alkyl, cyclo-alkyl, aryl, alkyl-aryl $C_1$–$C_{30}$ radical and R′ and R″ are the same and can be an alkyl, iso-alkyl, cyclo-alkyl, aryl or alkyl-aryl $C_1$–$C_{30}$ radical.

7. Composition according to claim 3, wherein the quantity of additives is between 0.001 and 1% by weight.

8. Composition according to claim 3, wherein the quantity of additives is between 0.005 and 0.15% by weight.

* * * * *